(12) United States Patent
Bernstein

(10) Patent No.: US 7,217,281 B2
(45) Date of Patent: May 15, 2007

(54) METHOD FOR DETECTING AND CORRECTING THE ROOT CAUSE OF HEALTH ISSUES

(76) Inventor: David M. Bernstein, 800 E. Cypress Creek Rd., Suite 100, Ft. Lauderdale, FL (US) 33334

( * ) Notice: Subject to any disclaimer, the term of this patent is extended or adjusted under 35 U.S.C. 154(b) by 212 days.

(21) Appl. No.: 10/610,222

(22) Filed: Jun. 30, 2003

(65) Prior Publication Data

US 2004/0267334 A1 Dec. 30, 2004

(51) Int. Cl.
*A61N 5/01* (2006.01)
(52) U.S. Cl. ....................................................... 607/89
(58) Field of Classification Search ............. 607/88–93
See application file for complete search history.

(56) References Cited

U.S. PATENT DOCUMENTS 5,199,876 A  4/1993  Waldman

OTHER PUBLICATIONS

Gaynor, L "Sound Body Recovery and Total Wellness"; Earth Star; Dec./Jan. 2003; pp. 19-23.*
Radomski, S "Energy Psychology Treatment of Allergy-like Reactions"; 2001: An Energy Odyssy—The Furigen Papers; William Lammers $ Beate Kircher, Eds.; Jun. 18, 2003 posting on:☐☐http://www.allergyantidotes.com.*
Jacobs et al.; "Diagnosis of Thyroid Dysfunction: Applied Kinesiology Compared to Cilinacl Observations and Laboratory tests"; J of Manipulative & Physiol. Therap.; vol. 7, No. 2; Jun. 1984; pp. 99-104.*

* cited by examiner

*Primary Examiner*—David M. Shay
(74) *Attorney, Agent, or Firm*—R. William Graham

(57) ABSTRACT

A method of detecting and correcting a debilitating causative factor of a health issue in a human system includes the steps of determining a debilitating causative factor in the human system and treating the human system by subjecting the human system to a low level laser having a deactivating frequency corresponding to the debilitating causative factor.

8 Claims, 3 Drawing Sheets

---

Determining a level of a condition using vials programmed to correspond to numerical values such that there is an increase in muscle strength in the right hand when the patient's left hand is in contact with a vial having a given frequency contained therein, this indicates a deactivating frequency to be set into the laser setting a low light laser with the predetermined deactivating frequency for a predetermined condition/causative factor Subjecting a Human System, which can include the patient's spine, having said condition/causative factor to the low level laser light at said frequency

US 7,217,281 B2

METHOD FOR DETECTING AND CORRECTING THE ROOT CAUSE OF HEALTH ISSUES

FIELD OF INVENTION

The present invention relates to the field of testing physiological conditions using electrical impulses. More particularly, the invention is directed to the use of glass vials that contain electromagnetic frequencies in a water-based solution that correspond to different anatomical parts, microorganisms, nutritional elements, toxins, symptoms and conditions. When the vials are placed within the human system's electromagnetic field, the health care practitioner can identify imbalances that are occurring within the human system and then use laser and or other prescribed therapy in response to the detection as a method of treating the same.

BACKGROUND OF THE INVENTION

Various forms of natural medicine exist today. Several forms of natural medicine which have received attention from the conventional modern scientific medical community as well as the natural medicine communities are acupuncture, kinesiology and reflexology. These forms of natural medicine address energy flow throughout a human system. This energy flow is often referred to as "subtle energy" which is drawn to systems of energy within and around the human system.

It is known in the fields of acupuncture, reflexology, and kinesiology that the body has so called biologically active points which can be treated, for example, with needles or with the application of pressure, to relieve tensions and normalize the functioning of internal organs and muscles. The locations of these treatment points, for example, on so called meridians, are well established and fixed.

The condition of a patient's internal organs and musculature can also be diagnosed to some extent by testing temperature and electrical skin resistance at the same biologically active points on the skin. Use of robes for sensing temperature and skin resistance are known. Subtle energy is similar or analogous to Qi (pronounced chi) of Chinese acupuncture and other natural healing techniques which focus on a universal life-force that is vital to the health of the mind and body of an organism.

Accordingly, natural medicine is being increasingly applied by doctors as well as natural therapists to a whole group of natural healing systems, which include these techniques. Subtle energy has always been seen and felt by healers and acupuncturists who are trained to read the flow of Qi through twelve specific pulses on the limb of a human body (a wrist). The pulse locations are connected with a series of energy pathways called meridians, each meridian relating to a specific organ, gland, or system of the organism.

In the field of kinesiology, a further connection has been made between meridians and specific muscles, with which the muscles are "energetically" connected Kinesiology uses manual muscle testing to assess the organism's energy and then applies a range of techniques to promote the healthy flow of energy throughout the human system. The philosophy of Chinese medicine is that health comes from being in balance and in harmony with all things, where balance is a perfect state in which no aspect is either deficient or in excess.

Energy circuits exist in organisms such as the human body and that energy fields extend to within two inches/five centimeters around the human system. The electromagnetic problems within an organism such as a human body are caused by electrical disturbances in these energy circuits which create poor or faulty communication with the human system, often giving rise to dis-ease (malfunction). It has been proposed that electromagnetic factors include: ionization which involves the balance of positive and negative ions that can be breathed in by an organism which create positive and negative currents within the organism; acupuncture meridians (energy pathways) which involve fourteen meridians for over-and under-energy, each relating to a specific part or parts of the human system; and right/left brain hemisphere integration.

Others explain that reflexology is a scientific technique of applying pressure to reflex areas or zones that have a definite affect on the normal functioning of all parts of an organism such as the human body. When properly performed, a reflex massage sends stimuli to various organs, glands, and nerves in the body. Tenderness at particular points, which are such as in the limbs of a body may indicate congestion of energy within the organism or body and that the reflexology promotes balance and normalization, to reduce tension, to revitalize, reactivate, regenerate, heal, and bring the whole system of an organism into harmony in a state of good health, naturally. It is thought that the human body is divided into ten areas of jurisdiction (meridians), where each area contains its corresponding organs with a reflex counterpart in the hand.

All structures have a natural resonant frequency, but can vibrate at dissonant frequencies. It is this nature of movement of energy which gives rise to harmonious or disharmonious, to the positive and negative aspects of health and environment.

The invention is aimed at providing a system which uses a file system comprised of a number of files and subfiles having predetermined digital response data which is indicative of a predetermined normal or predetermined abnormal condition in the human system. The file system is preferably computer based. The invention thus provides a diagnosis and treatment to promote energy flow in specific organs, glands, or systems within the human system through the synergistic combination of the tools resulting in digital response therapy.

SUMMARY OF THE INVENTION

It is an object to provide a unique method of quantitatively assessing health status and detecting and correcting the root cause of health issues.

It is another object to quantitatively assess the level of causative factor present in the compromised body part.

It is another object to provide to identify the causative factors (CF) that are blocking energy flow in the human system and remove them, so that the human system will reopen the lines of communication and restore regenerative healing energy to the involved area.

It is another object to promote healthy flow of energy throughout a person.

It is a further object of the present invention to provide a physically non-intrusive method of detection and correction that promotes healthy energy flow within the organism.

It is a further object of the present invention to provide a method of detection and correction which promotes healthy energy flow by substantially reducing energy imbalances within the human system.

These and other objects of the present invention are fulfilled by providing a method of detection and correction which promotes healthy energy flow for use in treating a patient. A method of detecting and correcting a debilitating causative factor of a health issue in a human system is provided. The method comprises the steps of determining a causative factor in the human system and treating the human system by subjecting the system to a low level laser having a deactivating frequency corresponding to the causative factor.

The step of treating is further characterized such that the deactivating frequency is derived from a digital response technique wherein the human system reacts to a frequency contained within a vial and wherein said frequency corresponds to a musical note. The vials are sequentially arranged and the deactivating frequency is determined by the vial that caused the patient's muscle to become strong. In particular, the deactivating frequency is determined by having the patient hold the causative factor vial in the left hand as his/her index finger of the same hand touches various sequentially arranged vials, each labeled with a specific electromagnetic frequency. When the patient touches the frequency labeled vial that causes the muscle in the patient's right hand to strengthen, the frequency contained in that vial is then set into the low level laser to treat the causative factor.

Further scope of applicability of the present invention will become apparent from the detailed description given hereinafter. However, it should be understood that the detailed description and specific examples, while indicating preferred embodiments of the invention are given by way of illustration only, since various changes and modifications within the spirit and scope of the invention will become apparent to those skilled in the art from this detailed description.

DETAILED DESCRIPTION OF THE PREFERRED EMBODIMENT

Figure 1:
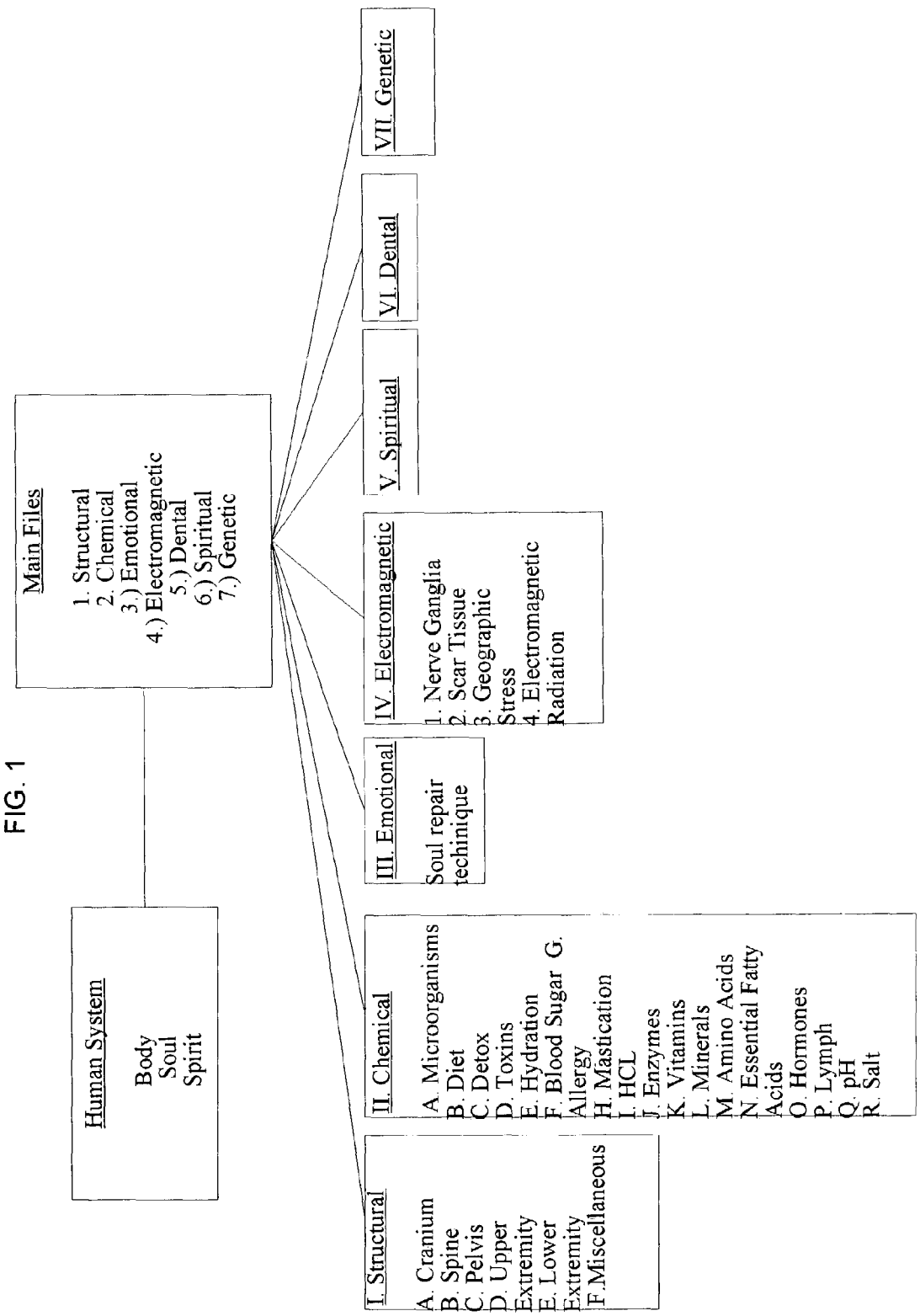
FIG. 1 is a schematic illustrating the human system broken down into various representative files and subfiles.

The method of correction and detection of the present invention will be better understood by the referring now to the drawings. There are several causative factors (CF) that create imbalanced energy flow. They are thought to at least include microorganisms, allergies, poor diet, toxins (heavy metals, pesticides, and chemicals), dental disorders, electromagnetic fields, scars and adhesions, physical trauma, emotional trauma, spiritual toxins, and genetic predisposition.

The human system is thought to include distinct but interactive components, i.e., a body (entire material or physical structure of a human organism), a soul (animating and vital principle in humans) and a spirit (that part pertaining to the Holy Spirit). Therefore, it is believed that the human system refers to the body, soul and spirit, all of which must be in balance and freely communicating in order to achieve optimum health.

There is an assumption that the human system is equipped with many functions that are similar to the workings of a computer. For purposes of the invention, the human system consists of a plurality of main files and sub-files which are listed under each of the main files. The files and subfiles correspond to particular characteristic of the subject human system. This filing system enables the practitioner of the invention to determine a root cause of all health issues. The main files include the following areas relating to the human system: Structural; Chemical; Emotional; Electromagnetic; Dental; Spiritual; and Genetic. These are broken into subfiles as follows:

I. Structural
   A. Cranium Cranial Sutures
   B. Spine
      1. Cervical
      2. Thoracic
      3. Lumbar
   C. Pelvis
      1. Sacrum
      2. Coccyx
      3. Pubic
   D. Upper Extremity
      1. Shoulder
      2. Elbow
      3. Wrist
      4. Fingers
   E. Lower Extremity
      1. Hip
      2. Knee
      3. Ankle
      4. Toes.
      5. Metatarsals
   F. Miscellaneous
      1. Bone
      2. Disk
      3. Muscle
      4. Tendon
      5. Ligament
      6. Cartilage
      7. Subluxation
      8. Dislocation
      9. Fracture
II. Chemical
   A. Microorganisms
      1. Mycoplasmas
      2. Fungi
      3. Bacteria
      4. Viruses
      5. Parasites
   B. Diet
   C. Detox
   D. Toxins—a. microorganisms b. metals c. bacteria d. viruses e. parasites
   E. Hydration
   F. Blood Sugar.
   G. Allergy
   H. Mastication
   I. HCL
   J. Enzymes
   K. Vitamins
   L. Minerals
   M. Amino Acids
   N. Essential Fatty Acids
   O. Hormones
   P. Lymph
   Q. pH
   R. Salt
III. Emotional—Soul repair technique
IV. Electromagnetic
      1. Nerve Ganglia
      2. Scar Tissue
      3. Geographic Stress
      4. Electromagnetic Radiation V. Spiritual VI. Dental VII. Genetic The present invention then employs a digital response technique (DRT) which is a sophisticated, yet easy to follow system, that consists of an expansive series of glass vials in order to determine the root cause of the health issue. Each vial is programmed with an electrical frequency that corresponds to a particular characteristic of each file or subfile. The vials are programmed with a particular frequency using an SE5 computer based machine which is equipped with a processor and means for charging a vial with a predetermined frequency for a given condition, state, organism etc. Such machines are currently known in the field of energetic medicine.

If a condition is known to exist, a treatment can be applied by using a laser treatment as is described herein after. For example, if a patient is known to have a small pox virus, the patient can be treated with low level line laser (soft laser) using a predetermined deactivating frequency for small pox.

Otherwise, a series of prescreening steps can be performed wherein the human system is subjected to a variety of pre-screening tests using vials which have been predetermined to have a frequency indicative or characteristic of one of the following:

1. Regulation
2. Switched
3. Overall Energy Flow
4. Liver Volume Capacity
5. Detox Pathway The subject patient can then subsequently be further tested using vials programmed with and an electrical frequency which has been predetermined to correspond to one of the main files, i.e., structural, chemical, emotional, electromagnetic, dental, spiritual, and genetic and subsequently tested with respect to each subfile within an identified file.

Figure 2:
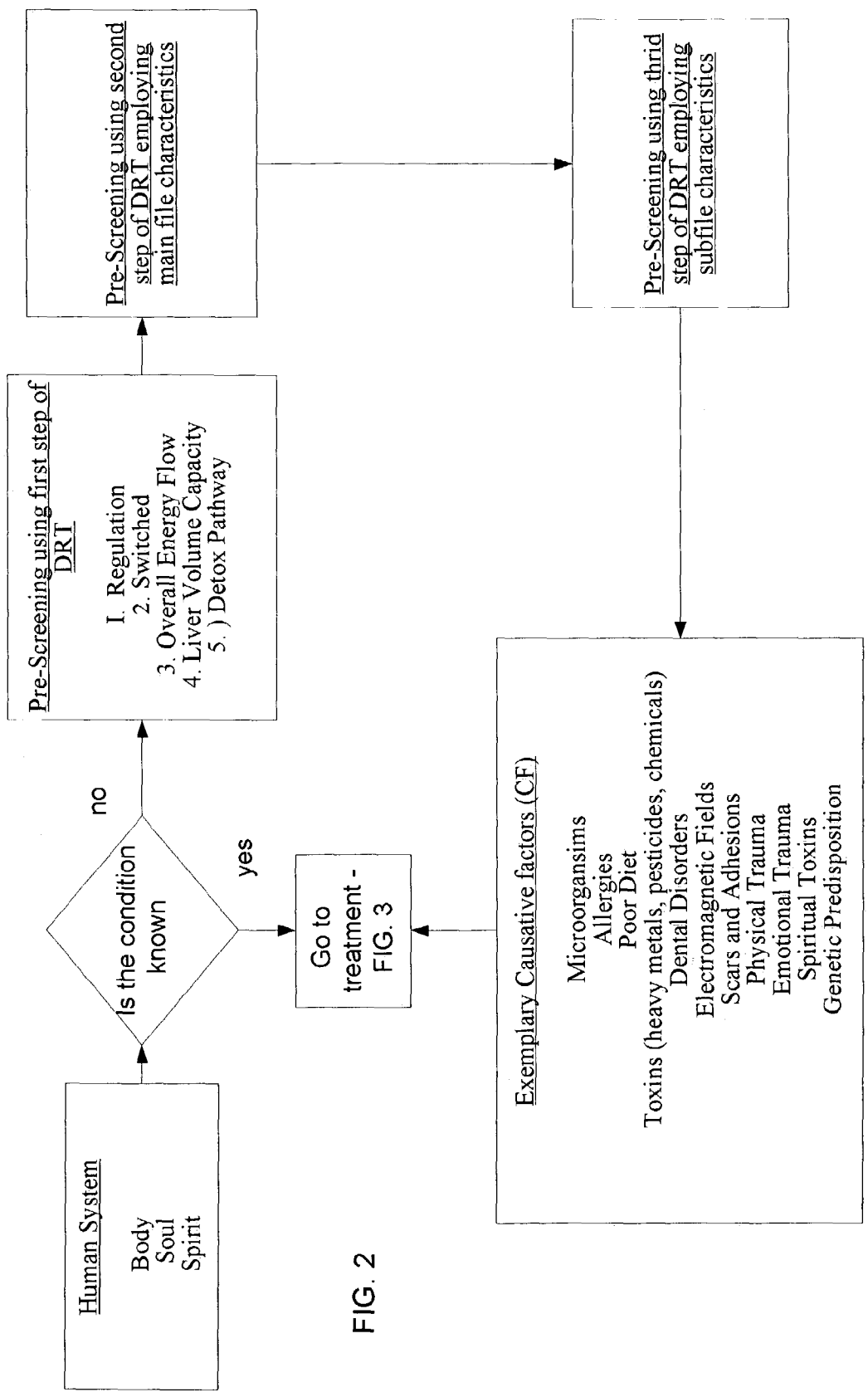
FIG. 2 is a schematic illustrating the human system employing detection methodology of the invention.
Figure 3:
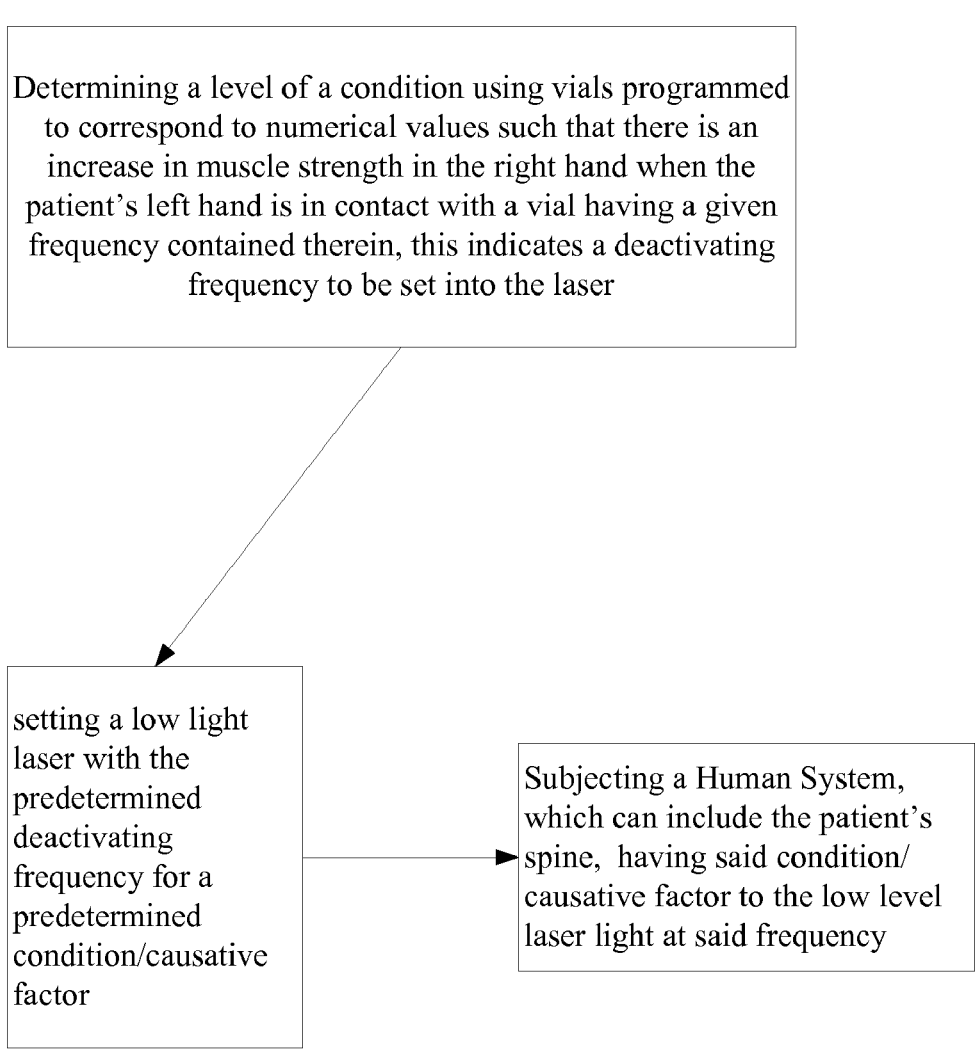
FIG. 3 is a schematic illustrating a treatment of the present invention.

The present invention requires that the patient hold a vial in his/her left hand as he/she touches the sequentially arranged series of vials with the same hand. As the patient touches each of the vials, the doctor tests the opponens muscle (thumb and pinky) of the opposite hand. The opponens muscle is used because it is more energy sensitive and less likely to fatigue than muscles tat involve the entire upper extremity. Each vial pertaining to a debilitating condition, or causative factor has a different frequency that is programmed by the SE5 machine. In addition, a set of vials pertaining to condition level ranging from 0–10 on a predefined scale in increments of 1 and a set of vials pertaining to condition level ranging from 0–0.9 in increments of 0.1 are provided which are likewise programmed a frequency by the SE5 machine. While holding the condition or causative factor vial(s), using the index finger of his/her left hand, the patient touches each numbered condition level vial sequentially, 0–10, until he/she reaches the vial that makes his/her right hand lock, i.e., become noticeably stronger. The patient then touches each decimal numbered vial sequentially, until he/she reaches the vial that makes the right hand lock. This indicates the level or amount of causative factor present. One of the main advantages of DRT is that it measures functional or useful energy rather than total energy. The invention looks for an increase in strength response by the muscular activity exhibited by the patient when holding the vial indicative of the presence of a causative factor. As seen in FIG. 2, the prescreening tests use a filtering mechanism to determine the causative factors.

Treatment of the patient to deactivate the causative factors can include:

Laser Technology;

Nutritional Supplementation;

Dietary Counseling;

Chiropractic Manipulation;

Soul Repair Technique (Emotional Clearing);

Spiritual Counseling;

Dental treatment; and/or

Health care practitioner referral as indicated from DRT.

Exemplary Initial Evaluation Procedure

Step 1. Determine Overall Health Index

The patient is provided the following three types of vials in his/her left hand, an overall health vial, a body, soul and spirit vial, and Subatomic, Atomic, Molecular, Cellular, Tissue (SAMCT) vial—which checks the energy 5 levels deep. Each type of vial has a different frequency which is given a frequency by the SE5 machine. In addition, a set of vials pertaining to condition level ranging from 0–10 on a predefined scale in increments of 1 and a set of vials pertaining to condition level ranging from 0–0.9 in increments of 0.1 are provided which are likewise given a frequency by the SE5 machine. While holding the other mentioned vials, using the index finger of his/her left hand, the patient touches each numbered condition level vial sequentially, 0–10, until he/she reaches the vial that makes his/her right hand lock, i.e., become noticeably stronger (e.g. 7). The patient then touches each decimal numbered vial sequentially, 0–0.9, until he/she reaches the vial that makes the right hand lock (e.g. 0.5). These two numbers taken together constitute the level of overall health index. In this case it would be 7.5. An ideal level is 10, which is 100% health, 7.5 means the client is functioning at 75% of his/her health potential.

Step 2. Regulation

The patient is provided the following two types of vials in his/her left hand, a regulation vial and an SAMCT vial. As before, using the condition level vials, the patient touches each numbered vial sequentially, as stated above in Step. 1, until he/she touches the vial that makes his/her right hand lock. If regulation is less than 10, it is blocked. Blocked regulation means that the client is dealing with a health issue that the autonomic nervous system finds so threatening that it draws energy from the various organ systems of the body in an effort to contain it. It causes such chaos in the nervous system that the practitioner will get inaccurate responses in his/her testing until the blocked regulation is dealt with. Therefore, regulation must be opened as soon as possible. A temporary means of opening regulation is by placing the vial that represents the causative factor of blocked regulation in contact with the client's body (e.g. place it in contact with the client's thigh) and then proceed with testing. Ideally, it is desirable to permanently correct the causative factor of blocked regulation as soon as your testing indicates the client's system is ready, willing and able.

Step 3. Switching

The patient is provided the following two types of vials in his/her left hand, a switched vial, and an SAMCT vial. As before, using the condition level vials, the patient touches each numbered vial sequentially, as stated above in Step. 1, until he/she touches the vial that makes his/her right hand lock. A reading of less than 10, indicates the patient is switched. This means that the messages are not flowing properly from one side of the brain to the other. This also needs to be corrected as soon as possible because it will yield inaccurate test results. A temporary means of correcting the switching phenomenon is by rubbing the medial aspect of the clavicle (where it meets the sternum) with one hand, as your other hand rubs the umbilicus in a circular motion for about 30 seconds. It is desired to permanently correct the switching issue as soon as testing indicates that the patient's system is ready, willing and able.

Step 4. Detox Pathways

The patient is provided the following two types of vials in his/her left hand, a detox pathway vial, and an SAMCT vial. As before, using the condition level vials, the patient touches each numbered vial sequentially, as stated above in Step. 1, until he/she touches the vial that makes his/her right hand lock. A reading of less than 10 indicates the patient has blocked detox pathways. This indicates that his/her exit doors (biliary system, urinary tract and digestive system) are not open all the way because there are too many toxins backed up in the system. Do not attempt to remove toxins or deactivate any microorganisms until the exit doors are completely open (10), otherwise toxins will get backed up as they try to exit the body and can cause significant detoxification symptoms.

A reading above 10 indicates the patient is detoxifying at a pace that is greater than his/her system is capable of handling. Attempt to remove toxins from the patient before his/her detoxification reading is a 10, you will place an additional toxic load on a system that is already overloaded. Typical detox symptoms include: (headaches, fever, runny nose, coughing, fatigue, brain fog, depression, etc.).

Step 5. Liver Volume Capacity

The patient is provided the following two types of vials in his/her left hand, a liver volume cap vial and an SAMCT vial. Here, the condition level vials range from 1–139. As before, using the condition level vials, the patient touches each numbered vial sequentially, as stated above in Step. 1, until he/she touches the vial that makes his/her right hand lock. This indicates how many pills the patient can safely handle in one day without overloading the liver. A reading of greater than 40 is ideal. A low level means that there is congestion in the liver.

Step 6. How Many Sites of Blocked Energy?

The patient is provided the following types of vials in his/her left hand, an overall health vial, a body, soul and spirit vial, and SAMCT vial. Here, the patient touches Core Level (initial DRT determined level), 2nd determined level, 3rd determined level, etc. to determine how many blocked areas there are. If the muscle becomes strong on Core Level but no other level, there is only one blocked area. If the client's muscle becomes strong on Core Level and 2nd Level, there are two blocked areas. If the client's muscle becomes strong on Core Level, 2nd Level and 3rd Level, there are three blocked areas in the body.

Step 7. Where are they?

Once it is determined how many sites of blocked energy there are, it is determined where they are as follows. The patient holds the SAMCT vial and Core Level vial and touches the Body Section vials starting at Cranium, Face, Neck, etc until the muscle strengthens. This is the location of the energy blockage. The client then touches each vial in the section of Organ System vials (Integumentary, Immune, Urinary, etc.) until he/she touches the one that makes the muscle become strong to determine which system in the body is involved. The patient then touches the various organ vials that are located in that section of the body in order to determine which organ is blocked.

Step 8. How's it Flowing?

To determine how much functional energy is flowing in the involved body part, the patient holds the following vials, the SAMCT vial, Organ (Body Part) vial and Regulation vial. As before, using the condition level vials, the patient touches each numbered vial sequentially, as stated above in Step. 1, until he/she touches the vial that makes his/her right hand lock. The combination of these two figures gives you the amount of functional energy flow through the involved body part. The ideal level is 10.

Step 9. How Many Causative Factors (CF)?

It is next determined how many causative factors are involved in the blocked energy to the involved body part. Often times there are more than one. The patient holds the Organ (Body Part) and SAMCT vials and touches Core Level, 2nd Level, 3rd Level, etc. The levels that cause a locking of the muscle show the number of causative factors.

Step 10. Who Done It?

Next, the causative factors (CF) are identified. To identify the first CF, the patient holds the following: Core Level, SAMCT and specific organ vials. The patient touches each of the Main File vials (Structural, Chemical, Emotional, etc.) until the muscle locks. Then test each of the sub-files until you reach the exact cause. For example, if the involved organ is the liver and it is found that the main file is Chemical, the sub-files are tested starting with Microorganisms. If the muscle becomes strong on Microorganisms, then the sub-files starting with Mycoplasmas, Fungus, Bacteria, Viruses, or Parasites are tested. If the muscle becomes strong on Viruses, then the virus vials are tested to determine the exact one.

If there is a second CF, the same procedure as above is repeated, except the patient holds a second Level vial instead of Core Level.

11. Optional Tests

The healthcare practitioner may elect to determine the energy flow through organs and organ systems in addition to the ones that showed in steps 1–10. The patient holds one of the following vials: specific organ (heart, kidney, lungs, etc.) or organ system (immune system, respiratory, endocrine system, etc.), in addition to Regulation and SAMCT.

Other miscellaneous elements to test for are Flora, Fiber, Gut Permeability, Hydration, Blood Sugar, HCL, Enzymes, Vitamins, Minerals, Amino Acids, Lymphatic Flow, Hormones, CIC (circulating immune complexes), Cortisol, Omega 3, Mercury, etc. The patient holds the appropriate miscellaneous vial and SAMCT vial to determine the level of each of these elements.

Exemplary Follow-Up Office Visit

Steps 1–5 are the basic preliminary steps that should be checked at the start of each visit. In this case, when checking the Detox Pathways, the patient holds the following Detox Pathway and SAMCT vials and if Detox Pathway is not completely opened (10), the invention calls for using a low level laser at 698.5 Hz on the liver, bowel and kidneys for 1.5 minutes total, based upon predetermined amounts as discussed below hereinafter. Further, the patient holds the Detox and SAMCT vials to see if Detox is greater than 10. If Detox is greater than 10, the lymph and the ganglia (nerve clusters that help to regulate the A.N.S.) are checked because toxins are backing up in either of these areas. The patient holds the following vials to check the lymph: Lymphatic vial and SAMCT vial. If lymph is less than 10, it has been predetermined to use the laser at 392 Hz on the liver, kidneys and bowel for 1.5 minutes total. The patient holds the following vials to check the ganglia: Ganglia vial and SAMCT vial. If ganglia reading is less than 10, it has been predetermined to use the laser at 247 Hz on the involved blocked ganglia.

Other pertinent findings from the previous office visit are than rechecked.

Laser Treatment For Deactivating Microorganisms

As indicated, if Detox Pathways are 10 and Detox is 10, then the patient may proceed to deactivate a detected microorganism, for example. The patient needs to be ready, willing and able (RW&A) to permanently deactivate the microorganism. The patient holds the following vials: RW&A vial, Appropriate Microorganism vial, and an SAMCT vial. If reading is less than 10, client does not want to get rid of this microorganism at this time. Check if an emotional issue is blocking patient from being RW&A to get rid of this microorganism. The patient holds the same vials as above and touches the emotional vial. If the muscle locks, an emotional issue is involved.

It is possible to clear the emotional issue using Soul Repair Technique (SRT), which is a form of DRT that determines and clears the root cause of an emotional issue. SRT clears the emotional issue by having the patient think about the earliest recollection of that emotion as well as a more current episode of that emotion while the health care practitioner applies a predetermined laser frequency to the patient's spine until the patient reaches a state where the said emotion is resolved. In other words, the patient is okay with the feelings connected to these incidents. If an emotional issue is not involved, do not address this microorganism because the patient is not physiologically prepared to release this bug and it could cause too severe a reaction. The client may need a few more treatments before he/she is ready. Only treat the microorganisms that have an RW&A reading of 10.

If RWA, a typical laser protocol consists of using a predetermined laser frequency(ies) to deactivate the microorganism(s) for 1.5 min. each, Lymph (392 Hz) for 1.5 min., Ganglia (247 Hz) for 1.5 min., Flora for (632 Hz) 1.5 min., and Organ System/ANS Balance (balances the autonomic nervous system flow through all the organ systems) (2093 Hz) for 30 sec.

The following exemplary deactivation laser frequencies have been predetermined by the inventor using the following technique. A vial pertaining to a particular condition or microorganism, for example, is held in the left hand of the patient afflicted with the same condition or microorganism. The patient also holds the SAMCT vial. The patient touches various vials, each of which contains a frequency that corresponds to a specific musical note, until the testing muscle becomes strong. The patient then holds that musical note vial (for example D) along with the microorganism vial and the SAMCT vial and touches various number vials to determine the precise octave of that note. For example, if the patient's muscle becomes strong on the number 6, the laser frequency to deactivate the microorganism is the 6$^{th}$ octave of D, which is 293.7. Below is provided a listing of some obtained deactivation frequencies.

| LASER/INFRARED DEACTIVATION FREQUENCIES (Hz) | |
|---|---|
| Aeromonas | 2959.9 |
| Amoeben | 1480 |
| ANS Balance/Organ Systems | 2093 |
| Bacteroides gingivalis | 2637 |
| Blastocystis hominis | 1108.7 |

| -continued | |
|---|---|
| LASER/INFRARED DEACTIVATION FREQUENCIES (Hz) | |
| CA Cells | 2349.3 |
| Chicken pox | 1244.5 |
| Chlamydia pneumonia | 2489 |
| CMV Envelope | 740 |
| CMV | 2489 |
| Cortisol | 932.3 |
| Coronavirus | 2959.9 |
| Coxsackie Virus | 659.3 |
| Detox | 698.5 |
| EGCG | 1244.5 |
| E. coli | 3951 |
| Enterovirus | 1480 |
| Epstein-Barr Virus Envelope | 740 |
| Epstein-Barr Virus | 2637 |
| Fleas | 2793.8 |
| Flu | 2489 |
| Fungus | 2217.4 |
| Fungus Toxins | 932.3 |
| Ganglia | 247 |
| Hemophilus influenza | 2959.9 |
| Hepatitis A | 2637 |
| Hepatitis B | 1108.7 |
| Hepatitis C | 2489 |
| Herpes I | 1480 |
| Herpes II | 1174.6 |
| Heliobacter pylori | 659.3 |
| Klebsiella | 2217.5 |
| Lamblia | 1174.6 |
| Lamblia Toxins | 1396.9 |
| Liver Fluke | 1396.9 |
| Lymph | 392 |
| Malassezia pachydermatis | 554.4 |
| Measles | 3951 |
| Mercury Detox | 1318.5 |
| Mold | 1244.5 |
| Mononucleosis | 2637 |
| Mumps | 2959.9 |
| Mycoplasma Envelope | 740 |
| Mycoplasma | 1396.9 |
| Mycoplasma pneumonia | 1975.5 |
| Nociceptors | 3136 |
| Pinworms | 622.3 |
| Polio | 1396.9 |
| Propionibacterium acnes | 2217.4 |
| Protozoa | 2959.9 |
| Pseudomonas aeruginosa | 1244.5 |
| Rubella | 3322.4 |
| Roundworm | 1396.9 |
| Scar Tissue | 698.5 |
| Shingles (Herpes zoster) | 880 |
| Smallpox | 1318.5 |
| Staph aureus | 2959.9 |
| Strep mutans | 1480 |
| Strep sanguis | 1568 |
| Strep viridans | 2349.2 |
| Suppressor Cells | 2793.8 |
| SV40 Virus | 1174.6 |
| Tapeworm | 1480 |
| Tapeworms Toxins | 261.6 |
| Tinea (ringworm) | 698.5 |
| Toxoplasmosis | 1568 |
| Vibrio | 1244.5 |

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their fill scope including any such modifications, derivations and variations.

What is claimed is:

1. A method of detecting and correcting a debilitating causative factor of a health issue in a human system, comprising the steps of:
   (a) determining a debilitating causative factor in the human system;
   (b) determining a level of a condition using vials programmed to correspond to numerical values; and
   (c) treating the human system by subjecting the human system to a low level laser having a deactivating frequency corresponding to said debilitating causative factor, wherein said step of treating is further characterized such that the deactivating frequency in said laser is derived from a digital response technique wherein the human system reacts to a frequency contained within one of said vials as determined by an increase in muscle strength in the human system when contact with such said vial indicating the frequency to be set into said laser to debilitate the causative factor.

2. The method defined in claim 1, wherein said step of treating is further characterized such that the deactivating frequency corresponds to a musical note the frequency of which is contained in said vial.

3. The method defined in claim 1, wherein said step of determining is derived from a digital response technique which includes sequentially placing in contact with the human system a plurality of vials each having a distinct frequency and pertaining to a type of causative factor such that when in contact with one of said vials causes a muscular reaction indicative of said debilitating causative factor.

4. The method defined in claim 1, wherein said human system holds said vial in a hand.

5. The method defined in claim 4, which is further characterized to be the use of one hand to hold said vial and said muscle strength is detected in the other hand.

6. The method defined in claim 3, wherein said human system holds said vial in a hand.

7. The method defined in claim 6, which is further characterized to be the use of one hand to hold said vial and said muscle strength is detected in the other hand.

8. The method defined in claim 1, which further characterizes the step of treating to include subjecting the spine of the human system to said laser.

* * * * *